US008771199B2

(12) United States Patent
Theobald et al.

(10) Patent No.: US 8,771,199 B2
(45) Date of Patent: Jul. 8, 2014

(54) FULL CORE BIOPSY NEEDLE WITH SECONDARY CUTTING CANNULA

(71) Applicant: Cook Medical Technologies LLC, Bloomington, IN (US)

(72) Inventors: Elizabeth A. Theobald, Bloomington, IN (US); James A. Taylor, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/650,279

(22) Filed: Oct. 12, 2012

(65) Prior Publication Data

US 2013/0041286 A1 Feb. 14, 2013

Related U.S. Application Data

(63) Continuation of application No. PCT/US2011/032043, filed on Apr. 12, 2011.

(60) Provisional application No. 61/323,912, filed on Apr. 14, 2010.

(51) Int. Cl.
*A61B 10/00* (2006.01)

(52) U.S. Cl.
USPC .......... 600/562; 600/563; 600/564; 600/565; 600/566; 600/567

(58) Field of Classification Search
USPC .......... 600/562, 564, 566, 567, 560, 563, 565
See application file for complete search history.

(56) References Cited

U.S. PATENT DOCUMENTS

| 4,991,592 | A | * | 2/1991 | Christ | 600/567 |
|---|---|---|---|---|---|
| 5,312,354 | A | * | 5/1994 | Allen et al. | 604/157 |
| 5,477,862 | A | * | 12/1995 | Haaga | 600/567 |
| 5,560,373 | A | * | 10/1996 | De Santis | 600/566 |
| 5,573,008 | A | | 11/1996 | Robinson | |
| 5,595,186 | A | * | 1/1997 | Rubinstein et al. | 600/567 |
| 5,655,542 | A | * | 8/1997 | Weilandt | 600/567 |
| 5,713,368 | A | * | 2/1998 | Leigh | 600/566 |
| 5,800,362 | A | * | 9/1998 | Kobren et al. | 600/564 |
| 5,885,226 | A | * | 3/1999 | Rubinstein et al. | 600/564 |
| 5,910,121 | A | * | 6/1999 | Paolo et al. | 600/562 |
| 6,022,324 | A | * | 2/2000 | Skinner | 600/566 |
| 6,050,955 | A | * | 4/2000 | Bryan et al. | 600/566 |
| 6,063,037 | A | * | 5/2000 | Mittermeier et al. | 600/567 |
| 6,261,243 | B1 | * | 7/2001 | Burney et al. | 600/564 |

(Continued)

FOREIGN PATENT DOCUMENTS

WO WO 2008/027829 A2 3/2008
WO WO 2009/036265 A1 3/2009

*Primary Examiner* — Rene Towa
*Assistant Examiner* — May Abouelela
(74) *Attorney, Agent, or Firm* — Woodard, Emhardt, Moriarty, McNett & Henry LLP

(57) ABSTRACT

There is shown and described embodiments of a biopsy needle that is simpler to make and use than existing devices. An inner and outer cannula are provided, with the outer cannula having a superelastic finger that lies along the length of the inner cannula in a retracted position and partially covers the lumen of the inner cannula in an extended position. The finger is pointed and in the form of a triangle in a particular embodiment, and does not extend beyond the outer extent of the inner cannula in the extended position.

23 Claims, 3 Drawing Sheets

(56) References Cited

U.S. PATENT DOCUMENTS

| | | | |
|---|---|---|---|
| 6,730,043 B2* | 5/2004 | Krueger et al. | 600/567 |
| 7,018,343 B2* | 3/2006 | Plishka | 600/564 |
| 7,160,292 B2* | 1/2007 | Moorman et al. | 606/33 |
| 7,828,773 B2* | 11/2010 | Swisher et al. | 604/162 |
| 8,088,081 B2* | 1/2012 | Field et al. | 600/567 |
| 8,187,203 B2* | 5/2012 | McClellan | 600/567 |
| 8,211,116 B2* | 7/2012 | Oostman et al. | 606/133 |
| 2001/0005778 A1* | 6/2001 | Ouchi | 600/564 |
| 2002/0058932 A1* | 5/2002 | Moorman et al. | 606/33 |
| 2006/0030785 A1* | 2/2006 | Field et al. | 600/567 |
| 2006/0089564 A1* | 4/2006 | Goldenberg | 600/566 |
| 2006/0122535 A1* | 6/2006 | Daum | 600/565 |
| 2007/0123800 A1* | 5/2007 | Nishtala et al. | 600/567 |
| 2007/0239064 A1* | 10/2007 | Cicenas et al. | 600/566 |
| 2008/0045857 A1* | 2/2008 | Miller et al. | 600/566 |
| 2008/0103458 A1* | 5/2008 | Rosiello | 604/272 |
| 2008/0228104 A1* | 9/2008 | Uber et al. | 600/567 |
| 2009/0069712 A1* | 3/2009 | Mulvihill et al. | 600/564 |
| 2009/0216152 A1* | 8/2009 | Speeg et al. | 600/567 |
| 2009/0240261 A1* | 9/2009 | Drews et al. | 606/133 |
| 2010/0004558 A1* | 1/2010 | Frankhouser et al. | 600/567 |
| 2010/0076342 A1* | 3/2010 | Miller | 600/567 |
| 2010/0217153 A1* | 8/2010 | Moos et al. | |
| 2010/0312140 A1* | 12/2010 | Smith et al. | 600/566 |
| 2011/0066074 A1* | 3/2011 | Weisman et al. | 600/566 |
| 2011/0082387 A1* | 4/2011 | Miller et al. | 600/567 |
| 2011/0208088 A1* | 8/2011 | Leimbach et al. | 600/567 |
| 2012/0059247 A1* | 3/2012 | Speeg et al. | 600/424 |
| 2012/0220894 A1* | 8/2012 | Melsheimer | 600/567 |
| 2012/0245487 A1* | 9/2012 | Eells et al. | 600/567 |

* cited by examiner

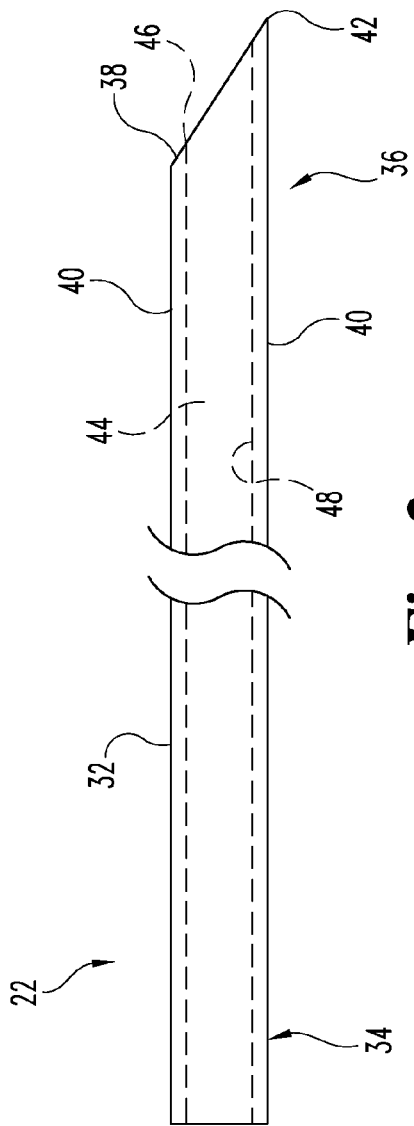
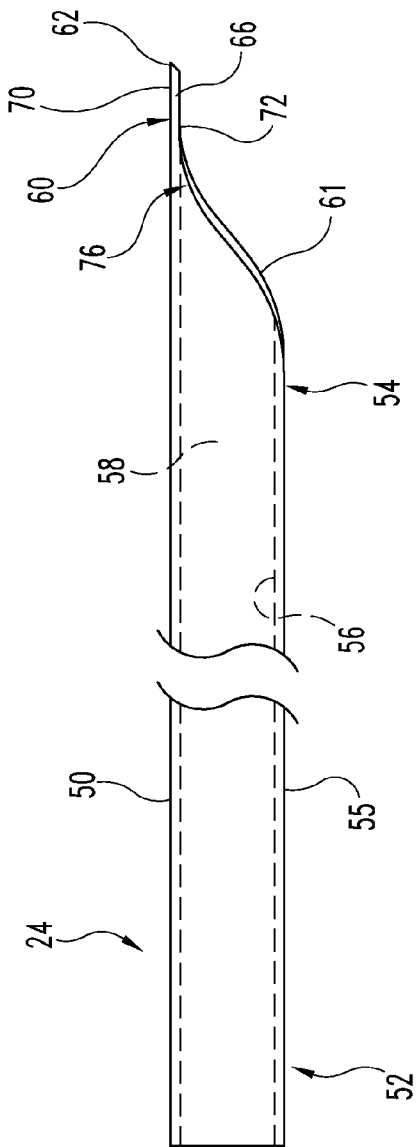

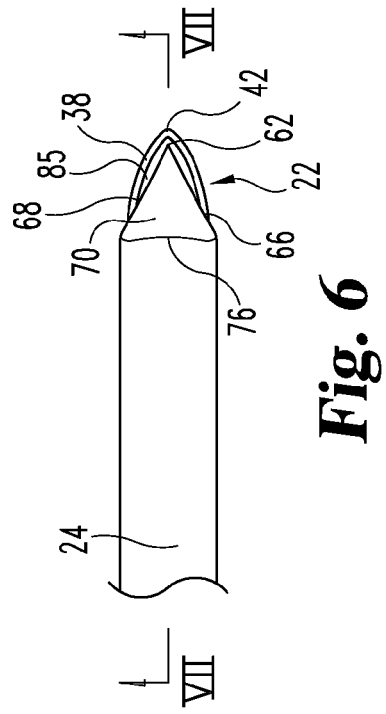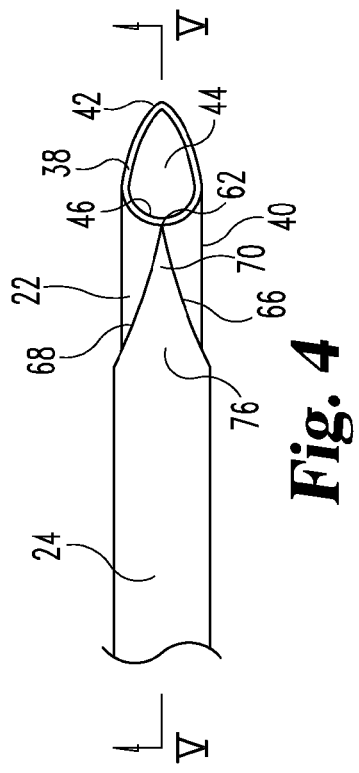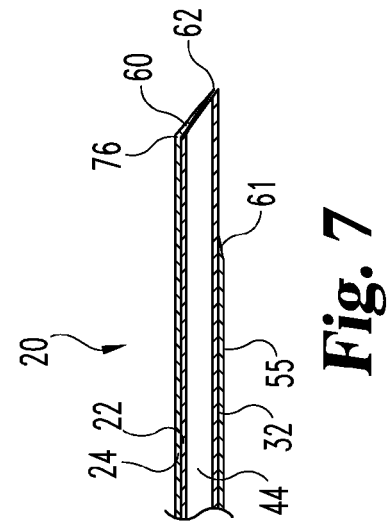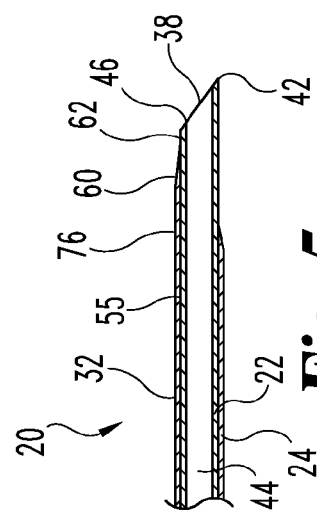

FULL CORE BIOPSY NEEDLE WITH SECONDARY CUTTING CANNULA

REFERENCE TO RELATED APPLICATIONS

This application is a continuation of International Application No. PCT/US2011/032043, filed Apr. 12, 2011, pending, which claims the benefit of U.S. Provisional Patent Application No. 61/323,912, filed Apr. 14, 2010, entitled FULL CORE BIOPSY NEEDLE WITH SECONDARY CUTTING CANNULA, both of which are hereby incorporated by reference.

This disclosure concerns devices for obtaining a tissue sample in biopsy. In particular, it concerns devices able to obtain a full-circular core of tissue with improved results over existing devices.

BACKGROUND

It is often desirable to perform a biopsy to sample selected tissue from a patient for medical evaluation. For example, biopsies can be useful in diagnosing various forms of cancer and other diseases affecting a localized area of tissue. However, many existing biopsy devices use only about half or less of their diameter to obtain tissue. Other devices that obtain a full cylinder or "full core" of tissue have difficulty in withdrawing tissue, and/or in maintaining the physical state of the tissue so as to provide an accurate assessment of tissue condition. With respect to the latter difficulty, one desire in obtaining tissue samples is to obtain the tissue with minimal physical changes, such as from scoring or mashing by the device. Physical characteristics of tissue, such as placement or orientation of cells or tissue, may be as important or more important than the chemical or biological characteristics (e.g. presence of malignant cells or by-products).

Accordingly, there is a need for a biopsy apparatus and method that are better able to provide samples that are easier to study.

SUMMARY

Among other things, there is shown and described a full-core biopsy needle that includes an inner cannula and a monolithic outer cannula. Embodiments of the inner cannula may have a full-tubular body and a sharpened distal end, defining a central lumen through the cannula and distal end. The distal end includes a substantially planar surface that is oblique to the longitudinal axis of the central lumen and around the central lumen. Embodiments of the outer cannula may have a tubular body with a substantially uniform outer diameter and defining a central lumen, with a distal end having a finger extending distally. At least the finger may have superelastic properties. The inner cannula is received within the central lumen of the outer cannula, with the cannulas being configured so that they are easily slidable with respect to each other and have a close fit at least at their distal ends. The cannulas have a first respective position in which the finger lies substantially along the inner cannula's oblique planar surface, but does not cover all of the inner cannula's central lumen and does not extend beyond the inner cannula's outer diameter or extent in particular embodiments. Some embodiments could have such a first respective position in which the finger covers all of the inner cannula's central lumen, extends beyond the inner cannula's outer diameter or extent. The cannulas have a second respective position in which the finger lies along the inner cannula's outer surface and does not extend over the oblique surface. In that second respective position, the finger is under greater stress than when it is in the first respective position, which stress biases the finger toward the inner cannula, and the finger does not extend beyond the outer diameter of the outer cannula.

In particular embodiments, the needle may have a handle connected directly to the inner cannula and the outer cannula. Such a handle may have a cocked state and an uncocked or fired state, such that the cannulas' second respective position corresponds to the cocked state, and the cannulas' first respective position corresponds to the uncocked or fired state. In some embodiments, the distal-most portion of the finger converges to a sharp point, and/or the finger has two sharpened sides that meet at that point. Those sides may be substantially linear, and the finger can be bendable around a bending axis, with the sides and said bending axis forming a triangle (such as an isosceles triangle). In some embodiments, the outer cannula up to the finger has a substantially uniform wall thickness that is a fraction of the wall thickness of the inner cannula.

In some embodiments, the outer cannula includes a bending axis around which the finger bends as the needle and its cannulas transition between the first (extended) respective position to the second (retracted) respective position, and the finger has a first thickness at the bending axis and a second smaller thickness at a distal-most point of the finger. That first thickness may be substantially the same as the wall thickness of the remainder of the outer cannula. The finger's decrease in thickness may be substantially linear. It may also have an underside that faces the inner cannula and is at least partially concave. A particular example of the positioning of the cannulas is where, when they are in the first (extended) respective position, the longitudinal axis through the center of the inner cannula's lumen intersects the finger, but the finger does not obstruct all of that lumen.

In other embodiments, a full-core biopsy needle may include an inner cannula defining a first lumen and having a wall of substantially uniform thickness bounding that lumen, as well as an outer cannula defining a second lumen in which the inner cannula has a close and slidable fit. The outer cannula has a body portion with a wall bounding its lumen that has a wall thickness less than that of the inner cannula's wall and a constant outer diameter. The outer cannula also has a finger projecting distally from the body portion and narrowing laterally to a point, with the finger adapted to bend with respect to the remainder of the outer cannula superelastically and around a bending axis. The outer cannula has a retracted position with respect to the inner cannula in which the finger between the bending axis and the point lies along the inner cannula so that the finger and at least the point is biased toward the longitudinal axis of the inner cannula. No portion of finger extends outside the outer diameter of the outer cannula's body portion.

In particular embodiments, the outer cannula is monolithic, and its finger is in a portion of the outer cannula that is non-interchangeable with respect to the rest of the outer cannula. The outer cannula has an extended position with respect to the inner cannula in which the narrowing finger at least partially covers the inner cannula's lumen including a central longitudinal axis of said lumen, and may leave side portions of the lumen open at the distal end. In the extended position, the finger's point may be within the inner cannula's outer diameter, or may not extend all the way across the inner cannula's lumen. In some embodiments the narrowing finger includes two sharpened sides, with the sides and bending axis substantially forming a triangle, such as an isosceles triangle. The cannulas may be connected directly to a handle that allows reciprocation of the cannulas with respect to each other. For example, when a handle is actuated to withdraw the outer cannula with respect to the inner cannula, the finger is withdrawn toward the retracted position.

These and other features may be found in a full-core biopsy needle as taught in this disclosure. Such needles are much simpler in construction than existing products. They are easier to manufacture and use without the complicated parts endemic to other devices, and provide less opportunity than other products for scoring or other injury to tissue along or adjacent to the biopsy path. The embodiments illustrated herein generate a larger core sample of tissue, and does so with a minimal diameter needle so as to decrease the width of biopsy path (and resultant tissue damage and discomfort) needed to obtain a desired width of tissue sample.

BRIEF DESCRIPTION OF THE DRAWINGS

FIG. 2 is a side plan view of an embodiment of an inner cannula as indicated in FIG. 1.

FIG. 3 is a side plan view of an embodiment of an outer cannula as indicated in FIG. 1.

FIG. 4 is a top view of a portion of the embodiment of FIG. 1.

FIG. 5 is a cross-sectional view of the portion in FIG. 4, taken along the lines V-V in FIG. 4 and viewed in the direction of the arrows.

FIG. 6 is a top view as in FIG. 4, showing a different relative position of the cannulas.

FIG. 7 is a cross-sectional view of the portion in FIG. 6, taken along the lines VII-VII in FIG. 6 and viewed in the direction of the arrows.

DESCRIPTION OF THE ILLUSTRATED EMBODIMENTS

Figure 8:
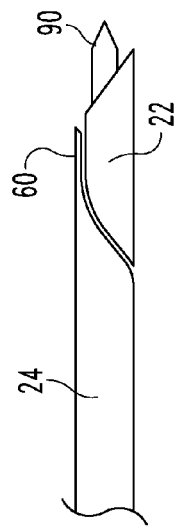
FIG. 8 is a side plan view of a portion of the device of FIG. 1 with additional structure.

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring now generally to the drawings, there is shown an embodiment of a biopsy needle 20. Needle 20 includes an inner cannula 22, and outer cannula 24 and a handle 26. Both inner and outer cannulas 22 and 24 are connected directly to handle 26 in this embodiment, i.e. without any connecting, opposing or intervening structure. As will be further explained below, needle 20 in this embodiment is particularly suited to subcutaneous full-core sampling, and may be used for obtaining multiple samples.

Inner cannula 22 is tubular in the illustrated embodiment, having an elongated body 32 extending between a proximal end 34 and a distal end 36. Elongated body 32 is at least substantially circular in the illustrated embodiment for ease of use and manufacture. Proximal end 34 is fixed to handle 26, as will be further discussed below. Distal end 36 is sharpened, for example by grinding a surface 38 that is planar and oblique to the longitudinal axis of cannula 22. Surface 38 meets external wall surface 40 of cannula 22 at a sharpened edge 42 that is at least at the forwardmost part of distal end 36. In particular embodiments, edge 42 comes to or approximately to a sharp or rounded point, indicated on the right or lower right end of cannula 22 in the drawings (see, e.g., FIGS. 1-2 and 4). Edge 42 may be sharpened around the lower portion of cannula 22 as viewed in FIGS. 1-2, such as the lower half of cannula 22, or the sharpening may extend further or all the way around cannula 22.

A lumen 44 extends through cannula 22 continuously and having a substantially uniform inner diameter from proximal end 34 to distal and 36. Oblique end surface 38 provides an opening for lumen 44 that is substantially elliptical and bordered by an edge 46 of inner wall surface 48 bounding lumen 44. Edge 46 is sharpened in the illustrated embodiment at least along a top portion (to the left of lumen 44 as viewed in FIG. 4), such as the top half of edge 46, and in other embodiments may be sharpened all the way around lumen 44. Lumen 44 is sized to be able to accommodate a desired diameter of full-core biopsy material. In particular embodiments, the gage of cannula 22 is between 10 and 20, such as 16, 18 and 20, so as to obtain a desired amount of tissue. The wall thickness of cannula 22 is preferably thin so as to slice through tissue and present a minimal profile. The minimal profile is found to reduce frictional or blunt-force damage to tissue samples.

The illustrated embodiment of outer cannula 24 is tubular, having an elongated body 50 extending between a proximal end 52 and a distal end 54. Elongated body 50 is at least substantially circular in the illustrated embodiment, having a cylindrical outer surface 55 and an inner cylindrical surface 56 defining a lumen 58, for ease of use and manufacture. Proximal end 52 is fixed to handle 26, as will be further discussed below. Tubular body 50 is cut at distal end 54 to form a tooth or finger 60. In the illustrated embodiment, an essentially planar oblique section is taken through cannula 24, so that a lower portion of cannula 24 (as seen in the Figures) ends at a more proximal location than side portions of cannula 24. That lower portion is essentially oblique in a forward orientation if oblique surface 38 is considered to be in a backward orientation, and is essentially open as viewed from finger 60. It thus presents less opportunity for interference with the tissue to be sampled. In the illustrated embodiment, the cut distal end 54 is beveled or otherwise shaped to an edge 61 so as to further minimize interference with tissue by moving it out of the way as outer cannula 24 is advanced.

Finger 60 is the most distal portion of cannula 24. Finger 60 has a sharpened point 62 that is the most-distal point of outer cannula 24, and finger 60 widens into the curvature of cannula 24 until the perpendicular cross section of cannula 24 forms a circle, as at location 64. In the illustrated embodiment, the widening (or tapering) of finger 60 is generally constant, so that respective side edges 66, 68 of finger 60 are generally linear as viewed from the top, at least until sides 66 and 68 begin to curve around the tubular surface of cannula 24. Sides 66, 68 converge in this embodiment to point 62 laterally. Upper surface 70 of finger 60 is a part of outer surface 55, and thus in this embodiment has a slight convex curvature. Lower surface 72 of finger 60 is an extension of inner surface 56. In the illustrated embodiment, lower surface 72 may have some concave portion, but is thinned steadily out to or toward point 62. In such an embodiment, surfaces 70 and 72 converge radially toward each other. Accordingly, in this embodiment, the thickness of finger 60 at point 62 is a fraction of the thickness of the wall of outer cannula 24, in some particular embodiments ¼ to ¾ of the wall thickness, and in one particular embodiment about ½ of the wall thickness. The thickness of finger 60 increases linearly (i.e. at a constant rate) until the thickness is the same as that of the wall of cannula 24. Lower surface 72, thinned as indicated above, becomes less curved and in particular embodiments may be substantially planar as surface 72 approaches point 62.

Finger 60, like the rest of this embodiment of cannula 24, is of a shape-memory material. Cannula 24 is prepared so that during use in the body, the material in at least finger 60 is in a superelastic state. While the tubular nature of cannula 24 retains body 50 in that form as stresses are applied, finger 60 is prepared so that it has an unstressed (or less-stressed) state (FIGS. 6-7) in which finger 60 crosses the longitudinal axis of cannula 24. Finger 60 can be elastically bent at a particular location or bending axis 76 to allow inner cannula 22 to be placed through cannula 24 to extend beyond finger 60 (e.g. FIGS. 4-5). In embodiments in which sides 66, 68 of finger 62 are generally linear, they may be considered with axis 76 to form a triangle. In the illustrated embodiment, sides 66, 68 with axis 76 form a substantially isosceles triangle. As will be further noted below, when stress on finger 60 is released, the superelasticity of the material of finger 60 returns it to or toward its unstressed state.

Handle 26 is fixed to each of cannulas 22 and 24 at their respective proximal ends, with inner cannula 22 within outer cannula 24 and the cannulas being slidable with respect to each other. An example of handle 26 that may be used in needle 20 is that currently used with QUICK-CORE® products sold by Cook Medical (Bloomington, Ind.). Embodiments of suitable handles are shown in U.S. Provisional Application No. 61/261,857, filed on Nov. 17, 2009, the entirety of which is incorporated herein by reference. Such handles 26 permit a cocking step in which outer cannula 24 is withdrawn or retracted with respect to inner cannula 22 (e.g. FIGS. 1, 4-5), an insertion step in which the relatively positioned cannulas 22, 24 are inserted into the body, and a firing step in which cannula 24 is released to move forward rapidly over inner cannula 22 and return to or toward the unstressed state. The cocking step is performed by holding finger grips 80 and pulling back on plunger 82. Inserting needle 20 is accomplished while holding finger grips 80 by forcing handle 26 (and connected cannulas 22, 24) forward without pushing on plunger 82. Firing cannula 24 is accomplished by pushing forward plunger 82 to overcome the cocked state, and may be accomplished by the same hand that holds finger grips 80.

Outer cannula 24 and inner cannula 22 are slidable with respect to each other, as indicated above. Inner cannula 22 extends from its connection with handle 26 through the lumen of outer cannula 24. In a particular embodiment, the outer diameter of inner cannula 22 is approximately the same as the inner diameter of outer cannula 24, so that there is little play or space between cannulas 22 and 24, yet they can move smoothly with respect to each other. Such close accommodation throughout the length of cannulas 22 and 24 also provide a benefit in the operation of finger 60.

Cannulas 22 and 24 have a first or extended relative position (FIGS. 6-7) which is seen before cocking or after firing needle 20. In that first relative position, finger 60 of cannula 24 is toward or in an unstressed condition. Finger 60 extends down along surface 38 of cannula 22 to cover at least a portion of the opening of lumen 44 of cannula 22. In the illustrated embodiment, the opening of lumen 44 is elliptical or oblong due to the circularity of lumen 44 and the oblique orientation of surface 38, and finger 60 has a substantially straight-sided configuration of a narrow angle emanating from point 62. Thus, in that embodiment finger 60 does not cover the entire area of the opening of lumen 44, or stated differently, when viewed end-on in this first relative position, the viewer can see at least a portion 85 (or two lateral portions) of lumen 44 past finger 60. Further, in this first relative position of the illustrated embodiment, point 62 does not extend past outer wall 55 of cannula 24, and in other embodiments point 62 does not extend beyond the opening of lumen 44, or extends to a location over oblique surface 38 between lumen 44 and outer wall 55. In other embodiments, finger 60 may be longer than shown in the illustrated embodiment, wider, rounded and/or otherwise shaped or configured so as to cover all of the opening of lumen 44.

Figure 1A:
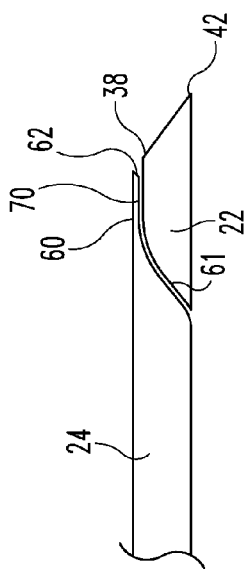
FIG. 1A is a close-up view of the portion of the embodiment of FIG. 1 indicated by the circle in FIG. 1.
Figure 1:
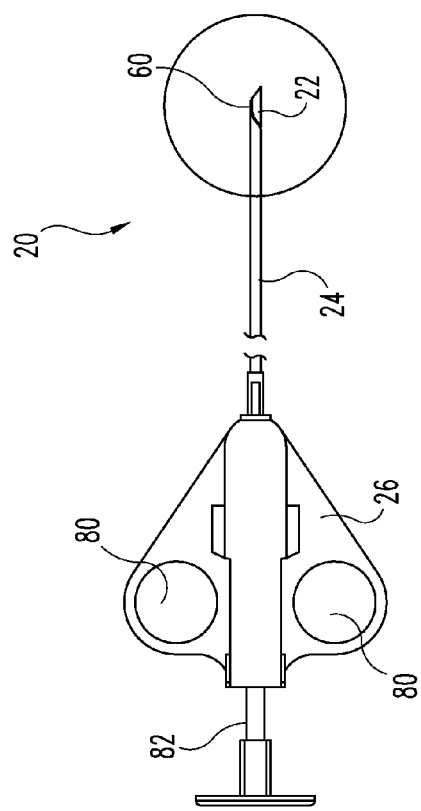
FIG. 1 is a plan view of an embodiment of a full-core biopsy needle.

When cannula 24 is withdrawn relative to cannula 22 (or cannula 22 is moved forward relative to cannula 24) from that first relative position, finger 60 is pushed upward by cannula 22. As indicated in FIGS. 6-7, at least a portion of surface 38 and outer surface 32 of cannula 22 engage the lower surface 72 of finger 60 as cannulas 22 and 24 move with respect to each other. That engagement is very close to axis 76 in the illustrated embodiment. Cannulas 22 and 24 have a second retracted relative position that corresponds to the cocked state of needle 20, in which point 62 is at or adjacent surface 38 of cannula 22 (FIGS. 1, 4-5). This particular configuration results in the advantage of a minimum amount of travel required for cannula 24 (or cannula 22) in order to cock and then to fire needle 20. While previous devices require a substantial distance of travel for an outer element, with the potential for scoring or otherwise damaging tissue it moves past, needle 20 reduces that distance of travel to a minimum in this embodiment, minimizing such damage and discomfort that accompanies it.

In this embodiment, surface 38 engages finger 60 at or next to its bending axis 76 to force finger 60 into a position along cannula 22. As noted above, finger 60 and the rest of cannula 24 are of a material exhibiting superelasticity, and therefore the stress placed on the bending axis 76 of finger 60 is held by finger 60, without breaking or damaging finger 60. By applying the force to bend finger 60 at or near the bending axis in the first instance, essentially as a class 3 lever, and maintaining contact of oblique surface 38 with lower surface 72 of finger 60 as cannulas 22, 24 move with respect to each other, finger 60 pivots around bending axis 76 easily with needed force decreasing as finger 60 bends. Finger 60 lays biased against outer wall surface 32 of cannula 22 in the second relative position. In this embodiment with a superelastic material for cannula 24, finger 60 lays against cannula 22 so that outer surface 70 of finger 60 and the rest of outer surface 55 of cannula 24 are substantially linear. That is, little or no bend or bulge exists at or adjacent bending axis 76 when finger 60 lays along cannula 22, and in particular embodiments no part of finger 60 extends outward of the outer diameter of body 50 of cannula 24. With that low profile, additional damage to tissue is reduced or eliminated, and no additional outer sleeve or similar device is needed through which to insert needle 20, since there is no or very little additional diameter of cannula 24 when finger 60 lays along cannula 22.

The use of needle 20 will now be described in the context of obtaining a sample of soft tissue for testing purposes. It will be understood that methods for obtaining samples of other tissues or for other purposes are also contemplated.

The surgeon or other medical professional first determines a location in a patient, with its depth under the skin, from which a tissue sample is desired. In one embodiment, cannulas 22 and 24 of needle 20 are in the relative position of FIGS. 6-7, in which finger 60 partially covers lumen 44 of cannula 22. In that state, the medical professional places distal end 36 of cannula 22 against the skin at a place proximate to the desired location, and inserts needle 20. Edge 42, in some embodiments, assisted by point 62 and/or sharpened edges

66, 68 of finger 60, force a path through the skin and subcutaneous tissue to a point in or just before the location from which a sample is to be taken. Upper surface 70 of finger 60, particularly in embodiments in which it has at least a slight convex curvature, tends to move tissue to the side rather than allowing it into lumen 44 during this insertion. The path size and shape is determined by the outer configuration of outer cannula 24, and with the relative thinness of cannula 24, the path is not substantially larger than the outer diameter of cannula 22, reducing discomfort from the biopsy procedure.

Needle 20 is cocked, as noted above, by pulling plunger 82 of handle 26 until it catches, resulting in moving outer cannula 24 backward over inner cannula 22. In the cocked state, in this embodiment, cannulas 22 and 24 are in the relative position indicated in FIGS. 1, 4 and 5, with finger 60 substantially linear with respect to the rest of cannula 24 and point 62 at or just behind oblique surface 38. Lumen 44 is open and oblique surface 38 and edges 42 and 46 are facing the tissue to be obtained, as is point 62.

Needle 20 is then moved forward an additional amount dictated by the amount of tissue to be obtained. With lumen 44 uncovered, that advancement results in cutting a profile (circular in the illustrated embodiment) through the tissue, with tissue entering lumen 44. When the amount of tissue desired is within lumen 44, the medical professional stops advancing needle 20, and fires cannula 24 forward by pressing plunger 82. As cannula 24 moves forward, point 62 remains biased against the outer surface 32 of cannula 22, and thus remains directed away from adjacent tissue outside needle 20 so as to minimize damage to that adjacent tissue as finger 60 moves forward. As finger 60 clears the edge between outer surface 32 and oblique surface 38 of cannula 22, the superelastic properties of finger 60 bend it back to or toward its unstressed or natural state. Point 62 and sharp edges 66, 68 cut a profile between tissue within lumen 44 and tissue outside lumen 44, and finger 60 covers at least a portion of lumen 44.

With cannulas 22 and 24 back in the extended relative position indicated in FIGS. 6-7, needle 20 is withdrawn. Finger 60 provides a back-stop to prevent tissue from sliding or being pulled out of lumen 44, and separation of the tissue inside lumen 44 from the remainder of the tissue is eased by the partial profile cut at the distal end of the tissue sample by the motion of finger 60 during firing. Point 62 does not extend beyond wall 55 in this embodiment, and so does not score or further damage tissue on withdrawal of needle 20. Embodiments of needle 20 can also provide better security for the sample with less cutting or physical damage to tissue. For example, when point 62 rests over surface 38 between lumen 44 and outer wall 55, no connection exists between tissue inside and tissue outside lumen 44 at a location directly below point 62, which would pull against point 62 in a direction perpendicular to bending axis 76 (potentially bending finger 60 back to some degree) when needle 20 is withdrawn. Similarly, any resistance by tissue connected to the sample through an opening 85 is not only counteracted by similar resistance on the other side, but it also acts in a direction such that only a component is perpendicular to axis 76 and so tends to bend finger 60. The configurations noted herein reduce or eliminate force tending to bend finger 60 and reopen lumen 44, with the risk of losing some or all of the sample in lumen 44.

Depending on the relative stiffness of part or all of finger 60, point 62 and the rest of finger 60 may describe an arcuate path as it moves to or toward its unstressed position. As finger 60 moves forward with respect to cannula 22, surface 32 holds finger 60 up until bending axis 76 approaches oblique surface 38. Finger 60 may swing or snap down against oblique surface 38, helping to push tissue into lumen 44.

It will be seen that needle 20 could also include a stylet 90 initially inserted through lumen 44 of cannula 22 (and through plunger 82 or other part of handle 26 if appropriate). Use of needle 20 in such an embodiment would be very much the same as noted above. With needle 20 cocked so that cannula 24 is withdrawn with respect to cannula 22, and finger 60 lies along cannula 22 in a stressed state, stylet 90 is present within lumen 44 so that an end of stylet 90 protrudes at least slightly from cannula 22. Needle 20 is inserted into the patient as described above, with stylet 90 occupying lumen 44 assisting to open a path to the biopsy location. When needle 20 is at or adjacent to the biopsy location, stylet 90 is removed to open lumen 44 to the tissue. Additional insertion, as noted above, forces cannulas 22 and 24 through tissue and tissue into lumen 44, and firing cannula 24 allows finger 60 to come down over lumen 44.

The superelastic and low-profile nature of needle 20 make taking multiple biopsy samples significantly easier and less traumatic. Once a first sample is taken, as discussed above, needle 20 may be moved further into the body along the path of insertion already made, or may be withdrawn from the body and reinserted at a different place. The steps noted above are repeated at the new location, so that the first tissue sample is forced proximally in lumen 44 as a second or further tissue sample is forced into the distal end of lumen 44. In this way, as many samples may be taken as are desired and as the length of lumen 44 will permit.

The present embodiment is arranged so that when outside cannula 24 is retracted (or assumes a retracted position by virtue of relative movement of cannulas 22 and 24), the force that moves finger 60 into its more-stressed and biased position along the length of inner cannula 22 is applied very close to the bending axis 76. By applying force close to the axis of rotation, torque is reduced and there is less likelihood of damage or inelastic bending at or adjacent the bending axis, which can result when bending forces are applied distant from a bending axis.

As noted above, inner cannula 22 has a close fit with outer cannula 24 within its lumen 58, and the two are slidable with respect to each other. By having both a "close fit" and slidability, it is meant that there is no substantial separation or gap between the cannulas, as by a boss or flange. As seen in the embodiments in the drawings, cannulas 22 and 24 have a close and slidable fit at least along their respective distal ends, and in some embodiments that close and slidable fit extends along all or substantially all of the cannulas' lengths. Such a configuration maximizes the amount of tissue obtained by a needle of particular outer diameter, by minimizing unused space in the needle, or conversely minimizes the external size of a needle needed to obtain a particular amount of tissue. Further, in describing an embodiment of cannula 24 as "monolithic," it is meant that the embodiment is a single item, not multiple items that float with respect to each other and/or are pushed by intermediate pieces. A monolithic cannula 24 as described above may be formed initially as a single piece from one material, with finger 60 being formed (as already noted) by grinding or cutting surfaces in the cannula. In another embodiment, a body 50 of cannula may be formed from one material and an end part with finger 60 may be formed from the same or a different material, and joined to body 50 in a fixed, permanent fashion. Such a monolithic or non-interchangeable character can prevent drifting or twisting of finger 60 with respect to inner cannula 22, which can occur if parts of cannula 24 are unfixed or interchangeable end.

It is noted that at least finger 60, and in some embodiments all of outer cannula 24, is of a superelastic material such as nitinol. It will be understood that a number of other materials exhibiting the characteristics noted above with respect to finger 60 could be used. The superelastic properties of outer cannula 24 or at least finger 60 provide for consistent elastic behavior to cut tissue, rather than mashing it, and to hold tissue within inner cannula 22, along with desirable thin profile of outer cannula 24. By reducing the thickness of cannula 24, cutting and holding of the sample is possible without significant increase in the overall outer diameter of needle 20. A larger sample can be obtained without a concomitantly larger outer profile and the increase in discomfort or potential hazard of interfering with undesired tissue on insertion.

It will also be noted that the distance of relative travel of cannulas 22 and 24 between the first (extended) relative position and the second (retracted) relative position is approximately the length between point 62 of finger 60 and bending axis 76. That short travel distance makes needle 20 easier to cock and quicker to fire. It also minimizes the potential for rubbing or scoring damage to internal tissue by travel of outer cannula 24 and finger 60, in addition to minimizing such potential through use of a superelastic finger biased against inner cannula 22.

This configuration provides a small but effective cutting surface and point on finger 60 that assist in insertion of needle 20 and cut through tissue to partially separate and hold the tissue within lumen 44 of cannula 22 from adjoining tissue, while not adding appreciably to the external diameter of needle 20. In the retracted state, no part of finger 60 presents a greater outer diameter or profile than any other part of outer cannula 24, because finger 60 pivots around axis 76 and remains biased toward the center of needle 20 when in the retracted state. The configuration reduces or eliminates crushing or other physical damage to the tissue sample and prevents significant additional damage (e.g. scoring or cutting) to unsampled surrounding tissue on actuation of the device and during its withdrawal from the patient.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected.

What is claimed is:

1. A full-core biopsy needle comprising:
an inner cannula having a sharpened distal end, defining a central lumen through said cannula and said distal end, said distal end including a substantially planar surface that is oblique to the longitudinal axis of said central lumen and around said central lumen; and
a monolithic outer cannula having a body with a substantially uniform outer diameter and defining a central lumen, with a distal end having a finger extending distally, at least said finger having superelastic properties, said inner cannula being received within said central lumen of said outer cannula, said inner cannula and outer cannula being configured so that they are easily slidable with respect to each other and have a close fit at least at said distal ends,
wherein said outer cannula and inner cannula have a first respective position in which said finger lies substantially over said oblique planar surface of said inner cannula but does not cover all of said oblique planar surface of said inner cannula and does not extend beyond the circumference at a distal-most point of the distal end of said inner cannula, and a second respective position in which said finger lies along the outer surface of said inner cannula and does not extend over said oblique surface,
wherein said finger does not extend beyond said outer diameter of said outer cannula and remains exterior to the distal end.

2. The needle of claim 1, wherein the distal-most portion of said finger includes two lateral edges that converge to a sharp point.

3. The needle of claim 2, wherein said edges are sharpened and linear to meet at said point.

4. The needle of claim 3, wherein said finger is bendable around a bending axis, and said edges and said bending axis form an isosceles triangle.

5. The needle of claim 1, wherein said outer cannula up to said finger has a substantially uniform wall thickness that is a fraction of the wall thickness of said inner cannula.

6. The needle of claim 1, wherein said finger has an underside that faces said inner cannula that is at least partially concave.

7. The needle of claim 1, where when said cannulas are in said first respective position, the longitudinal axis through the center of said lumen of said inner cannula intersects said finger, and said finger does not obstruct all of said lumen of said inner cannula.

8. The needle of claim 1, wherein the oblique planar surface encircles the lumen.

9. The needle of claim 1, wherein the finger is substantially flush against the oblique planar surface in the first respective position.

10. The needle of claim 1, wherein the superelasticity of the finger biases the finger toward the oblique planar surface in the first position.

11. A full-core biopsy needle, comprising: an inner cannula defining a first lumen, said inner cannula having a wall of substantially uniform thickness bounding said first lumen; and an outer cannula defining a second lumen in which said inner cannula has a close fit and said cannulas are slidable with respect to each other, said outer cannula having a body portion with a wall bounding said second lumen that has a wall thickness less than that of said inner cannula wall and a constant outer diameter, and a finger projecting distally from said body portion and narrowing laterally to a point, with said finger adapted to bend with respect to the remainder of said outer cannula superelastically and around a bending axis; wherein said outer cannula has a retracted position with respect to said inner cannula in which said finger between said bending axis and said point lies along said inner cannula so that said finger is biased toward the longitudinal axis of said inner cannula, and so that no portion of said finger is outside said outer diameter of said body portion of said outer cannula wherein said outer cannula has an extended position with respect to said inner cannula in which said narrowing finger partially covers said lumen including a central longitudinal axis of said lumen but leaving side portions of said lumen open at said distal end.

12. The needle of claim 11, wherein said outer cannula is monolithic, said finger being in a portion of said outer cannula that is non-interchangeable with respect to the rest of said outer cannula.

13. The needle of claim 11, wherein in said extended position, said point of said finger is within the outer diameter of said inner cannula.

14. The needle of claim 11, wherein in said extended position, said point of said finger is at a point between said lumen of said inner cannula and said outer surface of said inner cannula.

15. The needle of claim 11, wherein in said extended position, said point of said finger does not extend all the way across said lumen of said inner cannula.

16. The needle of claim 11, wherein said narrowing finger includes two sharpened side edges that meet at a sharp point, and said side edges and bending axis form an isosceles triangle.

17. The needle of claim 11, further comprising a handle connected directly to said inner cannula and said outer cannula to allow reciprocation of said cannulas with respect to each other, wherein when said handle is actuated to withdraw said outer cannula with respect to said inner cannula, said finger is withdrawn toward said retracted position.

18. The needle of claim 11, wherein the bias results from the superelastic finger.

19. A full-core biopsy device, comprising:
 an inner cannula having a proximal end, a distal end, an outer wall surface having a uniform outer diameter from said proximal end to said distal end, and a lumen defined by an inner wall surface, said lumen extending along a longitudinal axis and having a uniform inner diameter extending from said distal end toward said proximal end, said distal end having an end surface oblique to said longitudinal axis so that an opening of said lumen through said surface is oblong, wherein said outer wall surface and said end surface meet in a sharpened edge and said inner wall surface and said end surface meet in a sharpened edge;
 a monolithic outer cannula having a proximal end, a distal end, an outer wall surface, an inner wall surface defining a lumen, said inner cannula being slidable within the lumen of said outer cannula with said outer wall surface of said inner cannula closely facing said inner wall surface of said outer cannula
 wherein said distal end of said outer cannula forms a distally-pointing finger, said finger having an upper surface that is continuous with said outer wall surface of said outer cannula, said finger having a taper from a first width smaller than the outer diameter of said outer cannula to a point, said finger having at least a slight concave curvature on an underside facing said inner cannula, said finger being in a superelastic state,
 and wherein said outer cannula has a first position with respect to said inner cannula in which said point is proximal of said oblique surface and said finger is substantially parallel to said longitudinal axis, and a second position with respect to said inner cannula in which said finger is substantially parallel to said oblique surface and said point does not pass said edge formed by said outer wall and said oblique surface,
 and wherein when said inner cannula and said outer cannula are in said first position, said finger is biased by its superelasticity so that no portion of said finger is outside said outer diameter of said outer cannula.

20. The needle of claim 19, wherein the entirety of said outer cannula is a single tube of superelastic material.

21. The needle of claim 19, further comprising a handle connected directly to said inner cannula and said outer cannula.

22. The needle of claim 19, wherein said outer cannula has a maximum outer diameter of said outer wall surface in said second position, and in said first position no part of said finger is outside of said maximum outer diameter.

23. The needle of claim 19, wherein no substantial gap exists between said distal end of said inner cannula and said distal end of said outer cannula.

\* \* \* \* \*